United States Patent [19]

Gamble et al.

[11] Patent Number: 5,298,530
[45] Date of Patent: Mar. 29, 1994

[54] PROCESS OF RECOVERING COMPONENTS FROM SCRAP POLYESTER

[75] Inventors: William J. Gamble, Rochester; Andrius A. Naujokas, Webster; Bruce R. DeBruin, Rochester, all of N.Y.

[73] Assignee: Eastman Kodak Company, Rochester, N.Y.

[21] Appl. No.: 981,688

[22] Filed: Nov. 25, 1992

[51] Int. Cl.$^5$ ............................................. C08J 11/04
[52] U.S. Cl. ..................................... 521/48.5; 521/40; 521/48; 528/481; 528/496; 528/503
[58] Field of Search ...................... 521/40, 48, 48.5; 528/481, 496, 503

[56] References Cited

U.S. PATENT DOCUMENTS

| | | | |
|---|---|---|---|
| 3,037,050 | 5/1962 | Heisenberg et al. | 560/96 |
| 3,321,510 | 5/1967 | Lotz et al. | 560/96 |
| 3,776,945 | 12/1973 | Ligorati et al. | 560/96 |
| 4,163,860 | 8/1979 | Delattre et al. | 560/96 |
| 4,620,032 | 10/1986 | Doerr | 562/483 |
| 4,929,749 | 5/1990 | Gupta et al. | 560/79 |
| 5,051,528 | 9/1991 | Naujokas et al. | 560/78 |
| 5,095,145 | 3/1992 | Rosen | 562/483 |

FOREIGN PATENT DOCUMENTS

0484963A2 11/1991 European Pat. Off.

Primary Examiner—John Kight, III
Assistant Examiner—S. Acquah
Attorney, Agent, or Firm—David F. Janci

[57] ABSTRACT

A process of recovering components such as ethylene glycol and dimethylterephthalate from scrap polyester. The process steps are: (a) introducing oligomers of ethylene glycol and terephthalate acid or dimethyl terephthalate to a first vessel and heating the oligomers; (b) introducing scrap polyester to the first vessel and forming a startup melt with the oligomers; (c) transferring melt from the first vessel to a second vessel; (d) passing super-heated methanol through the melt in the second vessel to form a final melt comprising low molecular weight polyesters and monomers; (e) transferring final melt from the second vessel to the first vessel; and (f) recovering components from the second vessel.

8 Claims, 2 Drawing Sheets

PROCESS OF RECOVERING COMPONENTS FROM SCRAP POLYESTER

FIELD OF INVENTION

This invention relates to the recovery of components from scrap polyester such as polyethylene terephthalate. More particularly, it relates to a process of shortening the polyester chain lengths in a polyester scrap melt by contacting the scrap with a reactor melt prior to the introduction of scrap melt to the reactor.

BACKGROUND OF THE INVENTION

Polyethylene terephthalate polyester resins have found wide spread use in many and varied applications. For example, poly(ethyleneterephthalate) polyester resins find applications in the preparation of many types of films, including photographic film base, in fibers and in the preparation of food containers such as bottles and the like. Processes for recycling scrap polyester have been proposed. Various methods have been disclosed heretofore for the recovery of ethylene glycol and terephthalic acid or derivatives thereof which can be recycled and reused.

U.S. Pat. No. 5,051,528 teaches a process of recovering ethylene glycol and dimethylterephthalate from polyethyleneterephthalate scrap resins by dissolving the scrap polyester resin in oligomers of the same monomers as present in the scrap, passing super-heated methanol through the solution and recovering the ethylene glycol and dimethylterephthalate.

U.S. Pat. No. 4,620,032 teaches an extrusion process for reducing the reaction time in the hydrolysis of polyesters by intimately admixing with molten polyester a depolymerizing agent which is either one of the products resulting from the complete hydrolytic depolymerization of the polyester or water.

U.S. Pat. No. 3,776,945 teaches a process of depolymerizing polyethylene terephthalate waste to obtain dimethylterephthalate and ethylene glycol. The waste is subdivided into dimensions between 4 and 35 mesh and treated at a temperature of 100° C. to 300° C. and the presence of acid catalysts, the proportion of methanol to waste being between 1:1 and 10:1 by weight.

U.S. Pat. No. 3,321,510 relates to a process of decomposing polyethyleneterephthalate by treating with steam at a temperature of from about 200° C. to 450° C. The steam-treated polyethyleneterephthalate is then reduced from a brittle solid product to a powder having a mean particles size of from about 0.0005 to 0.002 millimeters, after which the fine powder is atomized with a gaseous substance including inert gas and methanol vapor to form an aerosol. The aerosol is conducted through a reaction zone at a temperature of 250° C. to 300° C. in the presence of excess methanol vapors.

U.S. Pat. No. 3,037,050 relates to the recovery of terephthalate acid dimethyl ester by treating polyethyleneterephthalate in the form of bulky or lumpy solid masses with super-heated methanol vapor in the presence of any suitable esterification catalyst substantially at atmospheric pressure.

EPA 484,963 teaches a process for recovery of dimethylterephthalate and glycols from polyester scrap that optionally provides a reactor solvent such as a mixture of methylhydrogenterephthalate and dimethyl terephthalate.

It can be seen from the above-recited art that many different techniques have been employed in the recovery of the monomeric constituents from polyesters. Such prior art techniques can either be too costly and inefficient or appropriate primarily for batch-type operation. A disadvantage of prior art processes using methanol is that solid scrap feed directly to the reactor can result in a risk of methanol vapor emission. Extrusion processes can have high operating costs and operate at high energy input levels. Thus, there is a widespread need for a simple, economical, continuous process of treating such polyesters to recover the initial ingredients utilized in the preparation of the polyester polymers or other useful recovery components.

SUMMARY OF THE INVENTION

The invention provides an improved process of recovering components from polyethyleneterephthalate, comprising the steps of:
(a) introducing glycol and terephthalic acid or dimethyl terephthalate oligomers to a first vessel and heating the oligomers;
(b) introducing scrap polyester to the first vessel and forming a startup melt with the oligomers;
(c) transferring melt from the first vessel to a second vessel;
(d) passing super-heated methanol through the melt in the second vessel to form a final melt comprising low molecular weight polyesters and monomers;
(e) transferring final melt from the second vessel to the first vessel; and
(f) recovering components from the second vessel.

In the continuous process of the invention, steps (c) through (f) are repeated, which allows scrap polyester to be fed to the first vessel while components can be recovered from the second vessel.

The invention provides a scrap polyester recovery process that solves the prior art problems described above. It is economical and safe to operate. It does not require an extrusion process. The process of the invention utilizes final melt product to promote the initial melting of the scrap polyester, which eliminates the need for an external source of reactant and results in a cost-effective, continuous recovery process.

DESCRIPTION OF THE PREFERRED EMBODIMENTS

Figure 1:
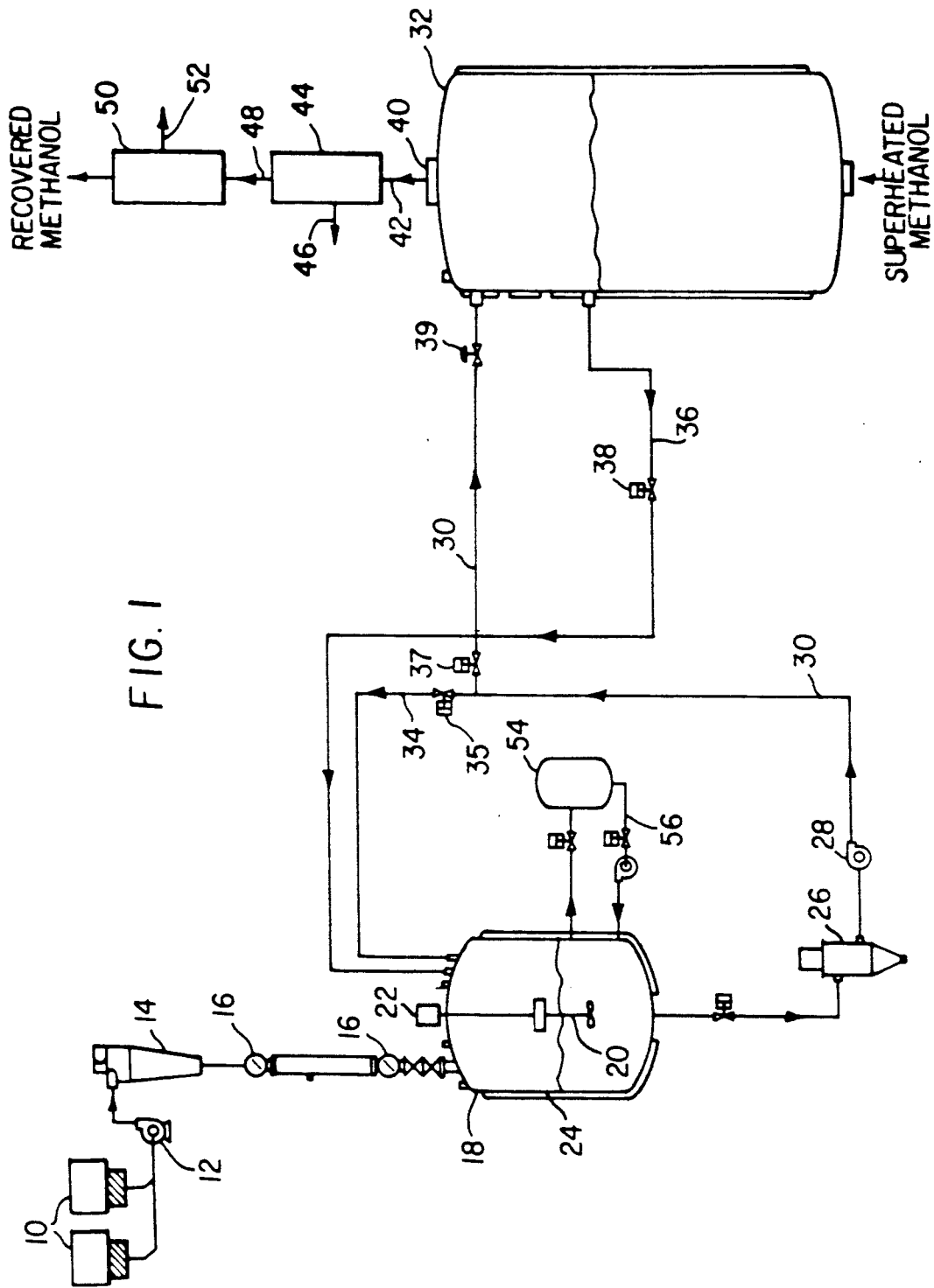
FIG. 1 is a schematic flow diagram illustrating an apparatus suitable for use in practicing the process of this invention.

FIG. 1 illustrates a representative system for practicing the process of the invention. Scrap polyethylene terephthalate is loaded into scrap bins 10, pumped by pump 12 to air conveyor 14, and conveyed through rotary air locks 16 to dissolver 18. Other convenient scrap polyester loading means such as screw feeders, extruders, or batch adders can alternatively be employed to supply the scrap polyester to dissolver 18. Dissolver 18 is equipped with agitator 20, driven by motor 22, and jacket 24 equipped with internal heating coils which is means for heating dissolver 18 and its contents. At startup, oligomers of a glycol such as ethylene glycol and dimethylterephthalate oligomers are introduced into dissolver 18 to at least approximately 5% of the volume of dissolver 18, and agitator 20 and jacket 24 are actuated to bring the temperature of the oligomers to a temperature in the range of from about 145° C. to about 305° C. A preferred such temperature range is from about 230° C. to about 290° C. The scrap polyethylene terephthalate and the oligomers are mixed in dissolver 18 for a time sufficient to allow the scrap polyethylene terephthalate to mix with the oligomers and form a startup melt. A preferred such mixing time at startup is from about 5 minutes to about 60 minutes.

The startup melt is drawn through strainer 26 and transferred by pump 28 via line 30 to reactor 32. Alternatively, the startup melt can be returned via return line 34 to dissolver 18, which is useful during startup, as well as after startup should it be desired, to provide molten polyester to the top of dissolver 18 to initiate melting of fresh polyester scrap feed. Valves 35, 37, and 39 are provided to adjust the flows accordingly.

Super-heated methanol vapor is provided to reactor 32 as shown schematically in FIG. 1. A conventional subsystem (not shown) can be provided to heat and supply the methanol to the reactor and to recover the methanol for reuse, such as the methanol supply and recovery loop described in U.S. Pat. No 5,051,528. The super-heated methanol vapor passes through the contents of reactor 32, heating the reactor contents to form a melt comprising low molecular weight polyesters and monomers, monohydric alcohol-ended oligomers, glycols, and dimethylterephthalate.

Reactor melt is transferred from reactor 32 and provided to dissolver 18 via line 36. The reactor melt reacts and equilibrates with the molten scrap polyester chains to shorten the average chain length, and thereby greatly decrease the viscosity, of the dissolver contents. Accordingly, the oligomers that are initially introduced into dissolver 18 are typically needed just at startup, and the process of the invention can be run continuously without having to further introduce external scrap polyester chain-shortening material to dissolver 18. This also simplifies the design of dissolver 18 and the associated apparatus. Dissolver 18 can be run at atmospheric pressure with little methanol present, greatly decreasing the risk of methanol leakage and increasing process safety. Simple solids handling devices such as rotary air locks 16 can be employed since more elaborate sealing devices are not necessary. The viscosity of the melt transferred from dissolver 18 is sufficiently low to permit the use of inexpensive pumping means, and permits reactor 32 to be operated at pressures significantly higher than atmospheric pressure.

Reactor 32 is preferably run at a higher pressure than dissolver 18, eliminating the need for pumping means to transfer reactor melt from reactor 32 to dissolver 18. Supplementary pumping means can optionally be provided if desired. Dissolver 18 can be run at about atmospheric pressure in the process of the invention. The operating pressure of reactor 32 can be in the range of from about 1 psig to about 100 psig. Reactor 32 is preferably operated at a pressure in the range of from about 30 psig to about 50 psig. The temperature of the melt in reactor 32 is preferably maintained above the boiling point of methanol for the pressure present in reactor 32 to maintain the methanol in the vapor state and allow it to readily exit from reactor 32. A preferred melt temperature in reactor 32 is in the range of from about 180° C. to about 305° C., and a melt temperature in the range of from about 250° C. to about 290° C. is particularly preferred. Valve 38 is provided to adjust flow through line 36 to a desired rate, which can be selected depending on the flow rates of material in and out of dissolver 18 and on the desired ratio of molten reactor contents to molten scrap polyester in dissolver 18. A preferred such ratio is from about 5 to about 90 weight percent reactor melt to scrap polyester, and a ratio of from about 20 to about 50 weight percent is particularly preferred. If desired, the recovery step (described below) can be deleted while reactor melt is transferred to the dissolver, for example, during standby operations when there is an interruption in the supply of scrap polyester to dissolver 18, during plant startup, or while the melt in dissolver 18 is brought up to operating levels.

A vapor stream comprising dimethylterephthalate, glycols including ethylene glycol, diethylene glycol, and triethylene glycol, dimethylisophthalate, cyclohexanedimethanol, methylhydroxyethyl terephthalate, and methanol exits reactor 32 via outlet 40 and line 42. The methanol is a depolymerization agent and the vapor aids in removal of the other vapors from the reactor by acting as a carrier gas stream and by stripping the other gases from solution. The effectiveness of the superheated methanol for heating the reactor contents and for stripping gases depends on its volumetric flow rate; the depolymerization rate in reactor 32 therefore depends on the methanol flow rate to reactor 32. Distillation device 44 can be optionally provided to separate methylhydroxyethyl terephthalate from the vapor stream exiting reactor 32 for recycling to the dissolver via line 46. Methylhydroxyethyl terephthalate is useful as a low molecular weight oligomer for shortening the average polyester chain length and decreasing the viscosity of the melt in the dissolver.

With or without distillation device 44, the vapor stream is transferred via line 48 to distillation device 50 which separates methanol from the other vapor stream components. The methanol can be recovered for further use as described in U.S. Pat. No. 5,051,528. The remaining recovered vapor stream components are transferred via line 52 to separation means (not shown) where the glycols are separated out. It may be desirable to provide lines 42 and 48 with heating means in order to prevent the condensation of any of the vapor stream components exiting from reactor 32.

The process of the invention may be carried out as a semi-continuous or continuous process. After initial startup, the startup oligomers described above do not have to be provided from a source external to the process; that is, the melt provided from reactor 32 and/or the methylhydroxyethyl terephthalate provided from optional distilling device 44 to dissolver 18 operate to shorten the average polyester chain length and sufficiently decrease the melt viscosity in dissolver 18.

Most contaminants are removed from the melt in dissolver 18 before introduction of melt to reactor 32. Inorganic contaminants such as metals or sand are removed by strainer 26. Polyolefins and other contaminants, such as polyethylene, polystyrene and polypropylene, that float on top of the melt in dissolver 18 are drawn off to separator 54 and separated out. Polyolefin-free melt is returned via line 56 to dissolver 18. Soluble contaminants can be allowed to accumulate in the melt in dissolver 18, which can be routinely purged with oligomers from reactor 32.

The invention will be illustrated by the following examples in which parts are by weight unless otherwise specified.

EXAMPLE 1

Figure 2:
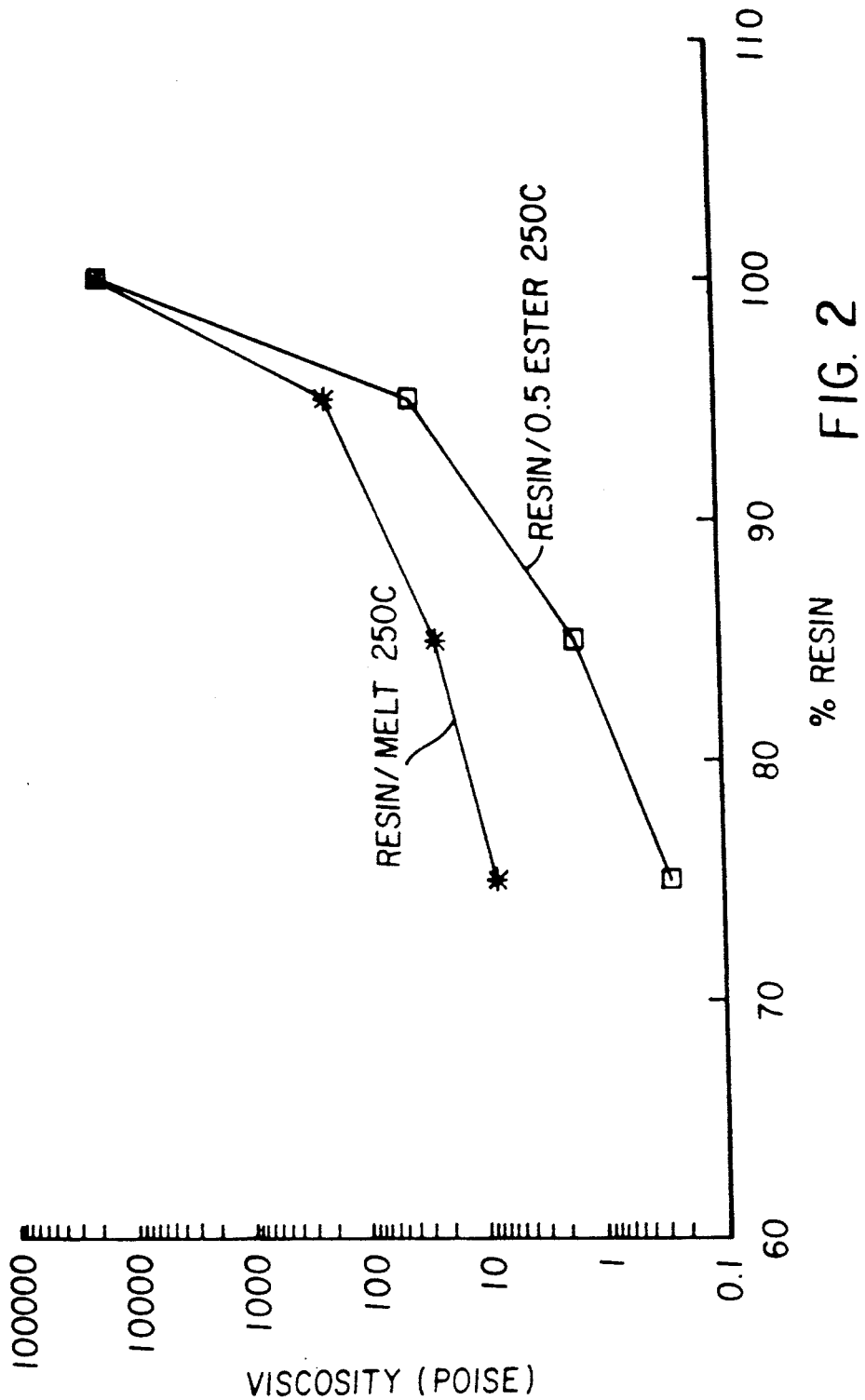
FIG. 2 is a graph of viscosity versus melt composition comparing viscosities of polyester scrap melt not mixed with reactor melt and polyester scrap melt mixed with reactor melt in the indicated proportions by weight.

A dissolver is charged with 2000 parts of polyethylene terephthalate oligomers containing a mixture having between 2 and 20 repeating units heated to about 250° C. to render the mass molten. Ground scrap polyethylene terephthalate bottles including polyolefin bottom cups, aluminum bottle caps, labels and any adherents used for the labels and bottom caps are fed to the dissolver at a rate of 2.5 parts/minute. The resultant dissolver melt is fed to a reactor and methanol is fed to the reactor at the rate of 20 parts by volume and sparged through the molten resin. The methanol, the glycols and the dimethyl terephthalate are recovered from a distillation column. A light layer of polyolefins can be skimmed off and aluminum collected at the bottom of the melt for removal from the dissolver. Reactor melt is returned to the dissolver as scrap polyester continues to be fed to the dissolver. Melt samples are drawn off from the dissolver and the viscosity of the samples are measured for dissolver mixtures having 5, 15 and 25 parts of reactor melt. The results are shown in FIG. 2. The viscosity of the melts containing reactor melt are significantly lower than the viscosity of the polyester melt without reactor melt mixed therewith.

As is evident from the foregoing description, certain aspects of the invention are not limited to the particular details of the examples illustrated, and it is therefore contemplated that other modifications and applications will occur to those skilled in the art. It is accordingly intended that the claims shall cover all such modifications and applications as do not depart from the true spirit and scope of the invention.

We claim:

1. A process of recovering components from scrap polyester comprising polyethylene terephthalate, comprising the steps of:
   (a) introducing glycol and terephthalic acid or dimethyl terephthalate oligomers to a first vessel and heating the oligomers;
   (b) introducing scrap polyesters to the first vessel and forming a startup melt with the oligomers;
   (c) transferring melt from the first vessel to a second vessel;
   (d) passing super-heated methanol through the melt in the second vessel to form a final melt comprising low molecular weight polyesters and monomers;
   (e) transferring final melt from the second vessel to the first vessel; and
   (f) recovering components in the form of a vapor stream exiting the second vessel.

2. The process of claim 1, further comprising the steps of repeating steps (c) through (f).

3. The process of claim 1, wherein steps (a) and (b) are conducted under atmospheric pressure.

4. The process of claim 3, wherein steps (a) and (b) are conducted under atmospheric pressure and steps (c) through (f) are conducted at a pressure in the range of from about 1 psig to about 100 psig.

5. The process of claim 1, wherein step (a) is conducted under atmospheric pressure, steps (c) through (f) are conducted at a pressure in the range of from about 30 to about 50 psig, and the temperature of the final melt is in the range of from about 250° C. to about 290° C.

6. The process of claim 1, further comprising the step of removing impurities from the contents of the first vessel.

7. The process of claim 1, wherein the components recovered in step (f) comprise glycols, dimethylterephthalate, cyclohexanedimethanol, dimethylisophthalate, and methylhydroxyethylterephthalate.

8. The process of claim 1, wherein after step (f) methylhydroxyethyl terephthalate is separated by distillation from the vapor stream exiting the second vessel and is transferred to the first vessel.

* * * * *